United States Patent [19]

Pohlke et al.

[11] Patent Number: 5,086,000
[45] Date of Patent: Feb. 4, 1992

[54] PROCESS FOR THE PREPARATION OF ALKYLENE-BIS(2-PYRIDYLAMINE) COMPOUNDS AND KARL FISCHER REAGENTS AND METHODS UTILIZING SUCH COMPOUNDS

[75] Inventors: Rolf Pohlke, Mühltal; Wolfgang Fischer, Darmstadt, both of Fed. Rep. of Germany

[73] Assignee: Merck Patent Gesellschaft Mit Beschränkter haftung, Darmstadt, Fed. Rep. of Germany

[21] Appl. No.: 616,132

[22] Filed: Nov. 20, 1990

[30] Foreign Application Priority Data

Nov. 21, 1989 [DE] Fed. Rep. of Germany .... 3938561.2

[51] Int. Cl.⁵ .................... G01N 33/18; C07D 213/36
[52] U.S. Cl. ................................. 436/42; 204/153.22; 546/264
[58] Field of Search ..................... 436/42; 204/153.22; 546/264

[56] References Cited

U.S. PATENT DOCUMENTS 3,656,907  4/1972  Delmonte ............................ 436/42

FOREIGN PATENT DOCUMENTS 0004217  3/1965  Japan .................................. 546/264

OTHER PUBLICATIONS

Sharp, J. Chrem. Soc., 1938, pp. 1191-1193.

*Primary Examiner*—Robert J. Hill, Jr.
*Attorney, Agent, or Firm*—Millen, White & Zelano

[57] ABSTRACT

The invention relates to a process for the preparation of alkylenebis(2-pyridylamine) compounds by reacting 2-halopyridine derivatives with alkylenediamines and to the use of these compounds in a Karl Fischer reagent as are indicated for the determination of water content.

8 Claims, No Drawings

PROCESS FOR THE PREPARATION OF ALKYLENE-BIS(2-PYRIDYLAMINE) COMPOUNDS AND KARL FISCHER REAGENTS AND METHODS UTILIZING SUCH COMPOUNDS

BACKGROUND OF THE INVENTION

The invention relates to a process for the preparation of alkylenebis(2-pyridylamine) compounds of formula I

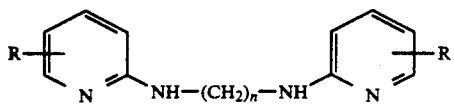

in which each R is independently H or $C_1$–$C_6$-alkyl and n is 2–8. The invention also relates to Karl-Fischer reagents containing a compound of the general formula I used for the determination of water content within a sample.

A preparation process for compounds of the general formula I is known from J. Chem. Soc. 1938, 1191–1193. There alkylenebis(2-pyridylamine) compounds are prepared by reacting 2-aminopyridine with dibromoalkanes in the presence of sodium amide in toluene as solvent.

However, the known synthetic process has a number of disadvantages. Thus, for example, the yields for lower alkylene radicals are unsatisfactory, the solvents used are a potential health risk and byproducts are formed which are very volatile and whose structure is not known.

SUMMARY OF THE INVENTION

The invention provides a new process for the preparation of alkylenebis(2-pyridylamine) compounds which does not have the disadvantages of the known process.

This invention also provides a reagent and method for determining the quantity of water in a sample which comprises a compound of formula I, sulfur dioxide and iodine.

Upon further study of the specification and appended claims, further objects and advantages of this invention will become apparent to those skilled in the art.

DETAILED DISCUSSION

It has been found that compounds of formula I are advantageously obtainable by reacting 2-halopyridine derivatives with an alkylenediamine. The yields in this process are excellent, and the workup is simple since only small amounts of byproducts are formed.

The invention, therefore, relates to a process for the preparation of alkylenebis(2-pyridylamine) compounds of formula I

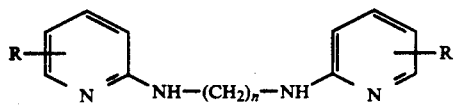

in which R is H or $C_1$ to $C_6$-alkyl and n is 2 to 8, wherein a 2-halopyridine derivative is reacted with an alkylenediamine.

The invention further relates to a Karl Fischer reagent containing a compound of the general formula I or a mixture thereof, sulfur dioxide and iodine for the determination of water content in a sample.

Suitable starting compounds for the process according to the invention are 2-halopyridine derivatives which may be substituted in the pyridine ring by alkyl groups.

Suitable alkyl groups are straight-chain or branched lower alkyl groups having 1 to 6 carbon atoms, for example methyl, ethyl, propyl, i-propyl, butyl, i-butyl, pentyl, i-pentyl, hexyl, i-hexyl. Suitable halogens are preferably chlorine and bromine, although the process can also be carried out with pyridines substituted by fluorine and iodine.

Suitable alkylenediamines are all straight-chain or branched α,ω-alkylenediamines having 2 to 8 carbon atoms, preferably those having 2 to 6 carbon atoms, such as ethylene-, propylene-, butylene-, pentylene-, hexylenediamine and isomers or mixtures thereof.

The process according to the invention is carried out in such a manner that about 0.6 to 0.9, preferably 0.75, moles of the alkylenediamine is combined with 1 mole of halopyridine derivative, and the mixture is heated to 140°–200° C. with stirring. After 15 to 20 hours, the reaction mixture is allowed to cool, and the mixture is poured into cold sodium hydroxide solution. The precipitate is filtered off with suction, washed with water, then stirred in an organic solvent in which the compound is insoluble, for example, a chlorohydrocarbon such as dichloromethane, and filtered off with suction. The product is recrystallized from a suitable polar solvent, for example an alcohol.

In the case of ethylenebis(2-pyridylamine) the yields are more than 4 times higher than according to the prior art, and in the case of hexylenebis(2-pyridylamine) the yield is quantitative. Accordingly, the present invention provides a very advantageous process for the simple high-yield preparation of alkylenebis(2-pyridylamine) compounds of the formula I.

The compounds of the formula I can be used successfully as substitutes for pyridine content in Karl Fischer reagents for the determination of water. Compared with the solutions containing pyridine, Karl Fischer solutions based on the compounds prepared according to the invention are odorless. The decrease in the titer of these solutions proceeds very slowly, that is to say, they are very stable and have shelf life of at least 2 years. The titrations using these Karl Fischer solutions proceed rapidly and have a stable end point.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of German P 39 38 561.2, filed Nov. 21, 1989, are hereby incorporated by reference.

EXAMPLE

Example 1

1.35 kg (11.88 mol) of 2-chloropyridine and 0.536 kg (8.92 mol) of ethylenediamine are heated at 150° C. for about 2.5 hours with stirring and maintained at this temperature overnight. The mixture is allowed to cool to 80°–90° C. and poured into 6 l of ice cold 8% sodium hydroxide solution with stirring. Stirring is continued for about another hour, the product is filtered off with suction and washed with 3 l of water. It is stirred in 1.5 l of dichloromethane, filtered off with suction, washed with 1.5 l of dichloromethane and recrystallized twice from 6 l each of isopropanol.

Yield: 0.765 kg (60%) of ethylene bis(2-pyridylamine), m.p. 132°–134° C.

Example 2

22.6 g (0.2 mol) of 2-chloropyridine and 17.4 g (0.15 mol) of 1,6-diaminohexane are heated at 180° C. for 20 hours. After cooling, the mixture is treated with sodium hydroxide solution, the precipitate is filtered off with suction, dried and recrystallized from isopropanol.

Yield: 22.0 g (81.5%) of hexylene bis(2-pyridylamine), m.p. 152°–154° C.

Example 3

31.6 g (0.2 mol) of 2-bromopyridine and 17.4 g (0.15 mol) of 1,6-diaminohexane are heated at 180° C. for 20 hours and worked up analogously to Example 2.

Yield: 27 g (100%) of hexylene bis(2-pyridylamine), m.p. 151°–153° C.

Example 4

Analogously to Example 1, 17.0 g (74.6) of propylene bis(2-pyridylamine) are obtained from 22.6 g of 2-chloropyridine and 11.1 g of diaminopropane. m.p. 118°–120° C.

Example 4 is repeated, using 31.6 g of 2-bromopyridine instead of 22.6 g of 2-chloropyridine, to give a yield of 15.3 g (67.1%).

Example 5

321 g of ethylene bis(2-pyridylamine)
128 g of liquid sulfur dioxide and
152 g of iodine are dissolved in succession in 1 l of diethylene glycol monomethyl ether with stirring and with the exclusion of moisture.

1 ml of the solution indicates 5.03 mg of water. When determining the water of a sample, 20 ml of methanol are titrated with the above reagent to the end point. The sample is then added, the solution is titrated again until a weak iodine color remains. The water content is calculated from the amount of solution consumed and the weight of the sample.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of alkylenebis(2-pyridylamine) compounds of formula I

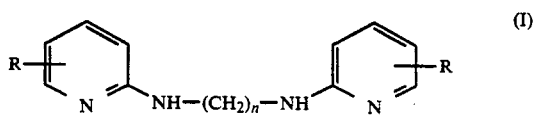

in which each R is independently H or $C_1$ to $C_6$-alkyl and n is 2–8, comprising reacting a 2-halopyridine or $C_1$ to $C_6$-alkyl derivative thereof with a corresponding alkylenediamine.

2. A process of claim 1, for the preparation of ethylene bis(2-pyridylamine) comprising reacting 2-chloropyridine with ethylenediamine.

3. A process as in claim 1, wherein the alkylene diamine is ethylenediamine, propylene diamine, butylene diamine, pentylene diamine, hexylene diamine, isomers thereof or mixtures thereof.

4. A process according to claim 1, wherein 0.6 to 0.9 moles of the alkylene diamine is used per mole of halopyridine compound.

5. A process of claim 1, carried out at 140°–200° C.

6. A process according to claim 5, wherein 0.6 to 0.9 moles of the alkylene diamine is used per mole of halopyridine compound.

7. In a method of determining the presence of water in a sample using a Karl Fischer reagent, the improvement comprising using as said reagent a compound produced in accordance with claim 5.

8. A Karl Fischer reagent for determining the presence of water in a sample comprising a compound of formula I of claim 1, sulfur dioxide and iodine.

* * * * *